(12) United States Patent
Bonde et al.

(10) Patent No.: US 6,210,902 B1
(45) Date of Patent: Apr. 3, 2001

(54) ESTIMATION OF THE FRAGMENTATION PATTERN OF COLLAGEN IN BODY FLUIDS AND THE DIAGNOSIS OF DISORDERS ASSOCIATED WITH THE METABOLISM OF COLLAGEN

(75) Inventors: Martin Bonde, Lyngby; Per Qvist, Klampenborg, both of (DK)

(73) Assignee: Osteometer Biotech A/S, Herlev (DK)

( * ) Notice: Subject to any disclaimer, the term of this patent is extended or adjusted under 35 U.S.C. 154(b) by 0 days.

(21) Appl. No.: 08/817,397

(22) PCT Filed: Oct. 16, 1995

(86) PCT No.: PCT/EP95/04055

§ 371 Date: Jun. 11, 1997

§ 102(e) Date: Jun. 11, 1997

(87) PCT Pub. No.: WO96/12193

PCT Pub. Date: Apr. 25, 1996

(30) Foreign Application Priority Data

Mar. 24, 1994 (GB) .................................................. 9506050

(51) Int. Cl.⁷ .................................................. G01N 33/53
(52) U.S. Cl. .................. 435/7.1; 435/7.92; 435/7.93; 435/7.94; 435/7.95; 436/518; 436/532; 530/356; 530/388.1; 530/389.1
(58) Field of Search ..................................... 435/7.1, 7.92, 435/7.93, 7.94, 7.95; 436/518, 532; 530/323, 326, 327, 328, 329, 356, 388.1, 389.1

(56) References Cited

U.S. PATENT DOCUMENTS

| | | |
|---|---|---|
| 3,600,132 | 8/1971 | Goverde . |
| 4,312,853 | 1/1982 | Timpl . |
| 4,504,587 | 3/1985 | Timpl et al. . |
| 4,628,027 | 12/1986 | Gay . |
| 4,778,768 | 10/1988 | Heinegard et al. . |
| 4,973,666 | 11/1990 | Eyre . |
| 5,001,225 | 3/1991 | Taylor . |
| 5,140,103 | 8/1992 | Eyre . |
| 5,300,434 | 4/1994 | Eyre . |
| 5,320,970 | 6/1994 | Eyre . |
| 5,455,179 | 10/1995 | Eyre . |
| 5,472,884 | 12/1995 | Eyre . |
| 5,473,052 | 12/1995 | Eyre . |
| 5,532,169 | 7/1996 | Eyre . |
| 5,576,189 | 11/1996 | Eyre . |
| 5,607,862 | 3/1997 | Eyre . |
| 5,641,837 | 6/1997 | Eyre . |
| 5,652,112 | 7/1997 | Eyre . |
| 5,656,439 | 8/1997 | Eyre . |
| 5,679,583 | 10/1997 | Brocks et al. . |
| 5,763,272 | 6/1998 | Naser et al. . |
| 5,821,065 | 10/1998 | Naser et al. . |
| 5,834,221 | 10/1998 | Eyre . |
| 5,912,131 | 6/1999 | Eyre . |
| 5,939,274 | 8/1999 | Eyre . |
| 5,962,639 | 10/1999 | Eyre . |

FOREIGN PATENT DOCUMENTS

| | | |
|---|---|---|
| 42 25 038 | 2/1994 | (DE) . |
| 0 298 210 | 1/1989 | (EP) . |
| 0 339 443 | 11/1989 | (EP) . |
| 0 394 296 | 10/1990 | (EP) . |
| 0 424 428 | 5/1991 | (EP) . |
| 0 465 104 | 1/1992 | (EP) . |
| 0 502 928 | 9/1992 | (EP) . |
| 0 505 210 | 9/1992 | (EP) . |
| 2 205 643 | 5/1987 | (GB) . |
| WO 83/04104 | 11/1983 | (WO) . |
| WO 88/08980 | 11/1988 | (WO) . |
| WO 89/04491 | 5/1989 | (WO) . |
| WO 89/12824 | 12/1989 | (WO) . |
| WO 90/04417 | 5/1990 | (WO) . |
| WO 90/08195 | 7/1990 | (WO) . |
| WO 91/08478 | 6/1991 | (WO) . |
| WO 91/09114 | 6/1991 | (WO) . |
| WO 92/21698 | 12/1992 | (WO) . |
| WO 94/03813 | 2/1994 | (WO) . |
| WO 94/14844 | 7/1994 | (WO) . |
| WO 95/04282 | 2/1995 | (WO) . |
| WO 95/08115 | 3/1995 | (WO) . |
| WO 96/30765 | 10/1996 | (WO) . |

OTHER PUBLICATIONS

International Search Report dated Feb. 15, 1995 of Int'l Appl. No. PCT/DK94/00348.

Ala–Kokko et al., 1989, "Structure of cDNA clones coding for the entire preproα1 (III) chain of human type III procollagen", *Biochem. J.* 260:509–516.

Ala–Kokko et al., 1990, "Single base mutation in the type II procollagen gene (COL2A1) as a cause of primary osteoarthritis associated with a mild chondrodysplasia", *Proc. Natl. Acad. Sci.* 87:6565–6568.

Baldwin et al., 1989, "Structure of CDNA clones coding for human type II procollagen", *Biochem. J.* 262:521–528.

Beardsworth et al., 1990, "Changes with age in the urinary excretion of lysyl– and hydroxylysylpyridinoline, two new markers of bone collagen turnover", *J. Bone Miner. Res.* 5:671–676.

Bernard et al., 1983, "Nucleotide Sequences of Complementary Deoxyribonucleic Acids for the Proα1 Chain of Human Type I Procollagen. Statistical Evaluation of Structures That Are Conserved during Evolution", *Biochemistry* 22:5213–5223.

(List continued on next page.)

Primary Examiner—Jeffrey Stucker
(74) *Attorney, Agent, or Firm*—Pennie & Edmonds LLP

(57) ABSTRACT

The fragmentation pattern of collagen, especially of type 1, as reflected in breakdown products of collagen in a body fluid such as serum or urine is estimated by measuring the levels of such breakdown products using two or more distinct immunoassays. The results may be combined into a numerical index diagnostic of one or more pathological conditions or patient types.

2 Claims, 4 Drawing Sheets

OTHER PUBLICATIONS

Black et al., 1988, "Quantitative analysis of the pyridinium crosslinks of collagen in urine using ion–paired reversed–phase high–performance liquid chromatography", *Ana. Biochem.* 169:197–203.

Black et al., 1989, "Urinary excretion of the hydroxypyridinium cross links of collagen in patients with rheumatoid arthritis", *Annals of the Rheumatic Diseases* 48:641–644.

Bonde et al., 1994, "Immunoassay for Quantifying Type 1 Collagen Degradation Products in Urine Evaluated", *Clin. Chem.* 40(11):2022–2025.

Bonde et al., 1995, "Measurement of Bone Degradation Products in Serum Using Antibodies Reactive with an 8 Amino Acid Sequence of the C–Telopeptides of Type I Collagen", *J. of Bone and Min. Res.* 10:1—Abstract S481.

Brennan et al., 1993, "Spontaneous degradation of polypeptides as aspartyl and asparaginyl residues: Effects of the solvent dielectric", *Protein Science* 2:331–338.

Capecchi et al., "Critical examination of a method for the analysis of a α and ω linkages in peptides containing aspartic acid and glutamic acid", *J. Org. Chem.* 48:2014–2021.

Christiansen et al., "Prediction of future fracture risk", eds, Proceedings 1993. Fourth International Symposium on Osteoporosis, Hong Kong. Osteopress Aps 1993; pp. 52–54.

Chu et al., 1984, "Human proα1 (I) collagen gene structure reveals evolutionary conservation of a pattern of itrons and exons", *Nature* 310:337–340.

Click et al., 1970, "Isolation and Characterization of the Cyanogen Bromide Peptides from the α1 and α2 Chains of Human Skin Collagen", *Biochemistry* 9:4699–4706.

de Wet et al., 1987, "Organization of the Human Pro–α2(I) Collagen Gene", *J. Biol. Chem.* 262:16032–16036.

del Pozo et al., 1986, "Binding of 1–anilinoaphthalene–8–sulfonic acid to type I collagen" *Int. J. Pept. Protein Res.* 28:173–178.

Delmas et al., 1986, "Serum Bone GLA–Protein in Growth Hormone Deficient Children", *J. Bone Min. Res.* 1:333–337.

Delmas, P.D., 1990, "Biochemical markers of bone turnover for the clinical assessment of metabolic bone disease", *Metabolic Bone Dis.* 19:1–18.

Dickson et al., 1993, "Pyridinolines and Cross–linked Type I Collagen N–telopeptides as Markers of Bone Metastases in Breast Cancer", 15th Annual Mtg of the Amer. Soc. for Bone & Min. Res., Tampa, Fl., Sep., 8:S288, Abstr. 686.

Dodge et al., 1989, "Immunohistochemical Detection and Immunochemical Analysis of Type II Collagen Degradation in Human Normal, Rheumatoid, and Osteoarthritic Articular Cartilages and in Explants of Bovine Articular Cartilage Cultured with Interleukin 1", *J. Clin. Invest.* 83:647–661.

Eyre et al., 1984, "Quantitation of Hydroxypyridinium Crosslinks in Collagen by High–Performance Liquid Chromatography", *Analytical Biochemistry* 137:380.

Eyre et al., 1988, "Identification of urinary peptides derived from cross–linking sites in bone collagen in Paget's disease", *J. of Bone & Mineral Res.* 3:S210, Abstr.565.

Eyre, D.R., 1984, "Cross–linking in Collagen and Elastin", *Ann. Rev. Biochem.* 53:717–748.

Eyre, D.R., 1994, "New Molecular Markers of Bone Metabolism", *Therapeutic Research (Symposium)* 15(2):532–535.

Fledelius et al., 1994, "Estimation of Bone Resorption Using Monoclonal Antibodies to Human Type I Collagen", *Am. Soc. of Bone and Min. Res.*, Abst. C344.

Fujimoto, D., 1980, "Evidence for natural existence of pyridinoline crosslink in collagen", *Biochem. & Biophys. Res. Comm.* 93:948–953.

Fujimoto et al., 1983, "Analysis of pyridinoline, a cross–linking compound of collagen fibers, in human urine", *J. Biochem.* 94:1133–1136.

Furthmayr, H., 1982, "Immunization procedures, isolation by affinity chromatography, and serological and immunochemical characterization of collagen specific antibodies", *Immunochemistry of the extracellular matrix*, H. Furthmayr (ed.), CRC Press, vol. 1, Chap. 11, pp. 143–178.

Galletti et al., 1995, "Protein damage and methylation–mediated repair in the erythrocyte" *Biochem. J.* 306:313–325.

Garnero et al., "Assessment of Bone Resportion with a New Marker of Collagen Degradation in Patients with Metabolic Bone Disease", *J. Clin. Endo. and Met.* 79(3):780–785.

Garnero et al., 1994, "Different Effects of Bisphosphonate and Estrogen therapy on the Excretion of Free and Peptide–Bound Crosslinks", *Amer. Soc. of Bone and Min. Res.*, Abst. 134.

Gertz et al., 1994, "Monitoring bone resorption in early postmenopausal women by an immunoassay for cross–linked collagen peptides in urine", *J. of Bone & Min. Res.* 9(2):135–142.

Gunja–Smith et al, 1981 "Collagen cross–linking compounds in human urine", *Biochem. J.* 197:759–762.

Hanson et al., 1992, "A specific immunoassay for monitoring human bone resorption: Quantitation of type I collagen cross–linked N–telopeptides in urine", *J. of Bone & Min. Res.* 7:1251–1258.

Hassager et al., 1994, "The carboxy–terminal pyridinoline cross–linked telopeptide of type I collagen in serum as a marker of bone resorption: The effect of nandrolone decanoate and hormone replacement therapy", *Calcif. Tissue Int.* 54:30–33.

Henkel et al., 1987, "Characterisation of a type–I collagen trimeric cross–linked peptide from calf aorta and it cross–linked structure", *Eur. J. Biochem.* 165:427–436.

Ishikawa, E., 1983, "Enzyme–Labeling of Antibodies and their Fragments for Enzyme Immunoassay and Immunohistochemical Staining", *Journal of Immunoassay* 4(3):209–327.

Janeczko et al., 1989, "Nucleotide and amino acid sequences of the entire human α1 (III) collagen", *Nucl. Acids Res.* 17:6742.

Kiviriko, K.I., 1979, "Urinary Excretion of Hydroxyproline in Health and Disease", *Int. Rev. Connect. Tissue Res.* 5:93–163.

Krane et al., 1981, "Organic Matrix Defects in Metabolic and Related Bone Diseases", *Develop. Biochem.* 22:185–194.

Kruger–Franke, 1991, "Pyridinoline–containing collagen degradation products in the urine of patients with osteoarthrosis of the hip joint", *Z. Rheumatol.* 50:323–327 (German with English Translation).

Kuboki et al., 1981, "Location of the intermolecular cross–links in bovine dentin collagen, solubilization with trypsin and isolation of cross–link peptides containing dihydroxylysinonorleucine and pyridinoline", *Biochem. & Biophys. Res. Comm.* 102:119–126.

Kuhn, K., 1982, "Chemical Properties of Collagen", *Immunochemistry of the Extracellular Matrix*, H. Furthmayr (ed.), CRC Press, 1(1)1–29.

Kuhn, K., 1987, "The Classical Collagens: Types I, II, and III", *Structure & Function of Collagen Types*, Mayne & Bergeson (eds.), Academic Press, pp. 1–42.

Kuypers et al., 1992, "Identification of the loci of the collagen–associated Ehrlich chromogen in type I collagen confirms its role as a trivalent cross–link", *Biochem. J.* 283:129–136.

Last et al., 1990, "Biosynthesis of collagen crosslinks", *Int. J. Biochem.*, 22(6):559–564.

Lehrman et al., 1992, "Identification and Characterization of an Anti–Isoaspartic Acid Monoclonal Antibody", *Journ. Of Prot. Chem.* 11(6):657–663.

Loidl et al., 1984, "Molecular cloning and carboxyl–propeptide analysis of human type III procollagen", *Nucl. Acids. Res.* 12(24):9383–9394.

Lowensen et al., 1988, Does the chemical instability of aspartyl and asparaginyl residues in proteins contribute to erythrocyte aging?, *Blood Cells* 14:103–117.

Macek et al., 1987, "Determination of collagen degradation products in human urine in osteoarthrosis", *Z. Rheumatol.* 46:237–240.

Morein et al., 1984, "Iscom, a novel structure for antigenic presentation of membrane proteins from enveloped viruses", *Nature* 308:457–460.

Morgan et al., 1970, "A Comparative Study of Glycopeptides Derived from Selected Vertebrate Collagens", *J. Biol. Chem.* 245:5042–5048.

Niemelä, O., 1985, "Radioimmunoassays for Type III Procollagen Amino–Terminal Peptides in Humans", *Clin. Chem.* 31(8):1301–1304.

Oliyai et al., 1994, "Chemical pathways of peptide degradation. VI. Effects of the primary sequence on the pathways of degradation of aspartyl residues in model hexapeptides", *Pharm. Res.* 11(5):751–758.

Otter et al., 1988, "Type I Collagen α–1 Chain C–Telopeptide: Solution Structure Determined by 600–MHz Proton NMR Spectroscopy and Implications for Its Role in Collagen Fibrillogenesis", *Biochem.* 27:3560–3567.

Otter et al., 1989, A $^1$H and $^{13}$C NMR Study on the Role of Salt–Bridges in the Formation of a Type 1β–Turn in N–Actyl–L–Asp–L–Glu–L–Lys–L–Ser–NH$_2$ *J. Biomol. Strut. Dyn.* 7(3):455–476.

Pierard et al., 1984, "Radioimmunoassay for the Amino–Terminal Sequences of Type III Procollagen in Human Body Fluids Measuring Fragmented Precursor Sequences", *Anal. Biochem.* 141:127–136.

Qvist et al., 1994, "Use of a New Biochemical Marker (Crosslaps™) for the Estimation of Rate of Postmenopausal Bone Loss", *Am. Soc. Bone and Min. Res. Abst. #B419.*

Rennard et al., 1980, "Enzyme–linked immunoassay (ELISA) for connective tissue components", *Anal. Biochem.* 104:205–214.

Riggs et al., 1992, "The Prevention and Treatment of Osteoporosis", *New England J. of Med.* 327(9):629–627.

Risteli et al., 1986, "Radioimmunoassay for Monitoring Connective Tissue Metabolism", *Rheumatol.* 10:216–245.

Risteli et al., 1993, "Radioimmunoassay for the pyridinoline cross–linked carboxy–terminal telopeptide oof type I collagen: A new serum marker of bone collagen degradation", *Clin. Chem.* 39:635–640.

Robins, S.P., 1982, "An enzyme–linked immunoassay for the collagen cross–link pyridinoline", *Biochem. J.* 207:617–620.

Robins et al., 1986, "Measurement of the cross linking compounds, pyridinoline, in urine as an index of collagen degradation in joint disease", *Annals of the Rheum. Diseases* 45:969–973.

Robins et al., 1987, "Measurement of the hydroxypyridinium crosslinks of collagen as an index of bone matrix degradation", Paper, Lake Garda, Italy, p. 23, Abstr. OP45.

Rodriguiz et al., 1993, "Type I Collagen cross–linked N–telopeptide excretion by osteopetrotic patients during interferon gamma therapy: A correlation with bone biochemical and densitometric markers", 15th Annual Mtg of the Amer. Soc. for Bone & Min. Res., Tampa, Fl., Sep., 8:5291, Abstr. 698.

Rohde et al., 1979, "Radioimmunoassay for type III procollagen peptide and its application to human liver disease", *Euro. Jour. of Clin. Invest.* 9:451–459.

Rohde et al., 1983, "Serum and urine analysis of the aminoterminal procollagen peptide type III by radioimmunoassay with antibody fab fragments", *Collagen Rel. Res.* 3:371–379.

Russell et al., 1981, "Biochemical Markers of Bone Turnover in Pagent's Disease", *Metab. Bone Dis. and Rel. Res.* 4 and 5, 255–262.

Sangiorgi et al., 1985, "Isolation and partial characterization of the entire human proα1(II) collagen gene", *Nucl. Acids Res.* 13(7):2207–2225.

Schröter–Kermani et al., 1990, "An Inhibition Elisa for the Quantification of Collagens Type I and Type II in Cyanogen Bromide–Digested Tissues Using Fragment–Directed Antibodies", *Immunol. Invest.* 19(5–6):476–491.

Schuppan et al., 1986, "Radioimmunoassay for the carboxy–terminal cross–linking domain of type IV (basement membrane) procollagen in body fluids", *J. Clin. Invest.* 78:241–248.

Scott, P.G., 1986, "Spectropic study of environment–dependent changes in the confirmation of the isolated carboxy–terminal telopeptide of type I collagen", *Biochem.* 25:974–980.

Seibel et al., 1989, "Urinary Hydroxy–pyridinium Crosslinks Provide Indices of Cartilage and Bone Involvement in Arthritic Diseases", *Journ. of Rheumatology* 16(7):964–970.

Singer et al., 1978, "Paget's Disease of Bone", *Metabolic Bone Disease* 2:489–575, (eds. Avioli, L.V. and Kane, S.M., Academic Press, New York).

Soinila et al., 1992, "Immunohistochemistry of Enkephalins: Models Studies on Hapten–Carrier Conjugates and Fixation Methods", *J. Hitochem. Cytochem.* (40)2:231–239.

Su et al., 1989, "Nucleotide sequence of the full length cDNA encoding for human type II procollagen", *Nucl. Acids Res.* 17:9473.

Tanaka, 1992, "Urinary excretion of β–aspartylpeptide in relation to collagen catabolism", Department of Agricultural Chemistry, Utsunomiya University, pp. 26–29 (Japanese and English translation).

Tanaka, 1995, "Urinary excretion of β–aspartylpeptide in relation to collagen catabolism", *Chem. Abstr.* 122:13797, abstr. 122:131800w.

Tellerova et al., 1986, "Determination of larger urinary peptides in osteoarthrosis by high–performance liquid chromatography", *Scand J. Rheumatol.* 15:52–56.

Uebelhart et al., 1990, "Urinary excretion of pyridinium crosslinks: a new marker of bone resorption in metabolic bone disease", *Bone and Mineral* 8:87–96.

Vikkula et al., 1989, "Structural analyses of the polymorphic area in type II collagen gene", *FEBS Lett.* 250:171–174.

Weiss et al., 1969, "The Quantitative Relationship of Urinary Peptide Hydroxypyroline Excretion to Collagen Degradation", *J. Clin. Invest.* 48:1–10.

Werkmeister et al., 1990, "Characterisation of a monoclonal antibody against native human type I collagen", *Euro. J. Biochem.*, 187:439–443.

Wu et al., 1984, "Identification of Hydroxypyridinium Cross–Linking Sites in Type II Collagen of Bovine Articular Cartilage", *Biochemistry* 23:1850–1857.

Ravn et al., 1994, "High Bone Turnover is Associated with Low Bone Mass in Both Pre–and Postmenopausal Women" *J. Bone and Min. Res.* 9(1) Abst. A216, p. S190.

Foged et al, 1994, "Bone Resorption In Vitro Characterized by ELISA" *J. Bone and Min. Res.* 9(1) Abst. B60, p. S245.

Bonde et al., 1994, "Crosslaps™ ELISA Plus—An Immunoassay for the Measurement of Degradation Products of Type I Collagen in Serum" *J. Bone and Min. Res.* 9(1) Abst. B178, p. S274.

Qvist et al., 1994, "Use of a New Biochemical Marker (Crosslaps™) for the Estimation of Rate of Postmenopausal Bone Loss" *J. Bone and Min. Res.* 9(1) Abst. B419, p. S334.

Overgard et al., 1994, "A New Biochemical Marker for Determination of the Optomum Treatment Regimen of Nasal Calcitonin and the Effect on Fracture Rates" *J. Bone and Min. Res.* 9(1) Abst. C342, p. S403.

Fledelius et al., 1994, "Estimation of Bone Resorption Using Monoclonal Antibodies to Human Type I Collagen" *J. Bone and Mn. Res.* 9(1) Abst. C344, p. S403.

Bonde et al., 1994, "An Immunoassay (Crosslaps™ ELISA) for Quantification of Type I Collagen Degradation Products in Urine" *J. Bone and Min. Res.* 9(1) Abst. C368, p. S406.

Bonde et al., 1995, "A Coated Tube Radio Immunoassay (RIA) for the Measurement of Bone Degradation Products in Urine Using a Monoclonal Antibody Reactive with an 8 Amino Acid Sequence of the C–Telopeptides of Type I Collagen" *J. Bone and Min. Res.* 10(1) Abst. S475, p. S269.

Poster of Bonde et al, 1995, *J. Bone and Min. Res.* 10(1) Abst. S475, p. S269 (Ref. FN).

Bonde et al., 1995, "Measurement of Bone Degradation Products in Serum Using Antibodies Reactive with an B Amino Sequence of the C–Telopeptides of Type I Collagen" *J. Bone and Min. Res.* 10(1) Abst. S481, p. S271.

Poster of Bonde et al., 1995, *J. Bone and Min. Res.* 10(1) Abst. S481, p. S71 (Ref. FP).

Fledelius et al., 1995, Effects of Anti–Resorptive Therapies on Two Immunoassays Specific for an B Amino Acid Sequence Found in Urinary Degradation Products from the C–Telopeptides of Type I.

Poster of Fledelius et al., 1995, *J. Bone and Min. Res.* 10(1) Abst. S482, p. S271 (Ref. FR).

Bonde et al., 1995, "Effect of Bisphosphonate Therapies (Pamidronate and Ibandronate) on the Excretion of Degradation Products of the C–Telopeptides of Type I Collagen Measured by a Radioimmunoassay (Crosslaps#RIA)" *Bone* 17(6) Abst. 45, p. 609.

Christgau et al., 1995, "Effect of Bisphosphonate Treatment on the Serum Concentration of Two Collagen Derived Biochemical Markers of Bone Metabolism" *Bone* 17(6) Abst. 48, p. 609.

Fledelius et al., 1995, "Effect of Bisphosphonate Treatment on the Urinary Excretion of C–Telopeptide Degradation Products of Type I Collagen Measured in the Crosslaps™ ELISA" *Bone* 17(6) Abst. 53, p. 611.

Ravn et al., 1995, "The Effect on Bone Mass and Bone Markers of Different Doses of Ibandronate—A New Bisphosphonate for Prevention and Treatment of Postmenopausal Osteoporosis, A 1–Year Randomized, Double–Blind, Placebo–Controlled Dose–Finding Study" *Bone* 17(6) Abst. 74, p. 616.

ESTIMATION OF THE FRAGMENTATION PATTERN OF COLLAGEN IN BODY FLUIDS AND THE DIAGNOSIS OF DISORDERS ASSOCIATED WITH THE METABOLISM OF COLLAGEN

This application is the national phase of international application PCT/EP95/04055 filed Oct. 16, 1995 which designated the U.S.

The present invention relates to a method of estimating the fragmentation pattern of collagen in body fluids. The invention further relates to analytical systems to be used when determining the collagen fragmentation pattern. Still further, the invention relates to the use of the above methods to diagnose and characterise the presence of disorders associated with the metabolism of bone.

Diseases of bone, among these osteoporosis, are becoming an increasing burden to society. The total cost in the USA in 1992 of osteoporosis related injuries alone is estimated to be at least USD 10 billion (Riggs, New England Journal of Medicine, 327:620–627 (1992)).

Osteoporosis as well as a number of other diseases of bone are characterised by an increased rate of bone loss when compared to the rate of loss in a healthy population. The rate of loss has been shown to be highly correlated to the future fracture risk (Christiansen et al., Prediction of future fracture risk. In: Christiansen et al., eds, Proceedings 1993. Fourth International Symposium on Osteoporosis, Hong Kong. Osteopress Aps 1993; pp. 52–54). Therefore the rate of loss is an important parameter to estimate for the diagnosis of such diseases.

In order to assess the rate of loss the estimation of the rate of bone resorption plays a key role. Even though the rate of loss is the net difference between the bone formation and bone resorption rates, markers of the bone resorption alone have proved to be good estimates of the rate of loss (Bonde et al. "Immunoassay for Quantifying Type 1 Collagen Degradation Products in Urine Evaluated" Clin. Chem. 40/11, 2022–2025 (1994)—Endocrinology and Metabolism. The estimate of bone loss is improved, however, by including also markers of bone formation (Qvist et al. American Society of Bone and Mineral Research, Abstract # B 419, Kansas City, 1994).

In the past, assays have been developed for monitoring degradation of collagen in vivo by measuring various biochemical markers, some of which have been degradation products of collagen.

For example, hydroxyproline, an amino acid largely restricted to collagen, and the principal structural protein in bone and all other connective tissues, is excreted in urine. Its excretion rate is known to be increased in certain conditions, notably Paget's disease, a metabolic bone disorder in which bone turnover is greatly increased, as discussed further below.

For this reason, urinary hydroxyproline has been used extensively as an amino acid marker for collagen degradation; Singer, F. R. et al., Metabolic Bone Disease, Vol. II (eds. Avioli, L. V., and Kane, S. M.), 489–575 (1978), Academic Press, New York.

U.S. Pat. No. 3,600,132 discloses a process for the determination of hydroxyproline in body fluids such as serum, urine, lumbar fluid and other intercellular fluids in order to monitor deviations in collagen metabolism. The Patent states that hydroxyproline correlates with increased collagen anabolism or catabolism associated with pathological conditions such as Paget's disease, Marfan's syndrome, osteogenesis imperfecta, neoplastic growth in collagen tissues and in various forms of dwarfism.

Bone resorption associated with Paget's disease has also been monitored by measuring small peptides containing hydroxyproline, which are excreted in the urine following degradation of bone collagen; Russell et al., Metab. Bone Dis. and Rel. Res. 4 and 5, 2250262 (1981), and Singer, F. R., et al., supra.

In the case of Paget's disease, the increased urinary hydroxyproline probably comes largely from bone degradation; hydroxproline, however, generally cannot be used as a specific index for bone degradation. Much of the hydroxyproline in urine may come from new collagen synthesis (considerable amounts of the newly made protein are degraded and excreted without ever becoming incorporated into tissue fabric), and from turnover of certain blood proteins as well as other proteins that contain hydroxyproline.

Furthermore, about 80% of the free hydroxyproline derived from protein degradation is metabolised in the liver and never appears in the urine. Kiviriko, K. I., Int. Rev. Connect. Tissue Res. 5:93 (1970), and Weiss, P. H. and Klein, L., J. Clin. Invest. 48:1 (1969). Hydroxyproline is a good marker for osteoporosis as it is specific for collagen in bones even if it is not specific for bone resorption, but it is troublesome to handle.

Hydroxylysine and its glycoside derivatives, both peculiar to collagenous proteins, have been considered to be more accurate than hydroxyproline as markers of collagen degradation. However, for the same reasons described above for hydroxyproline, hydroxylysine and its glycosides are probably equally non-specific markers of bone resorption; Krane, S. M. and Simon, L. S., Develop. Biochem. 22:185 (1981).

Other researchers have measured the cross-linking compound 3-hydroxypyridinium in urine as an index of collagen degradation in joint diseases. See, for back-ground and as examples, Wu and Eyre, Biochemistry, 23:1850 (1984): Black et al., Annals of the Rheumatic Diseases, 45:969–973 (1986); and Seibel et al., The Journal of Dermatology, 16:964 (1989). In contrast to the present invention, these prior researchers have hydrolysed peptides from body fluids and then looked for the presence of free 3-hydroxypyridinium residues.

Assays for determination of the degradation of type I, II, and III collagen are disclosed in EP-0394296 and U.S. Pat. No. 4,973,666 and U.S. Pat. No. 5,140,103. However, these Patents are restricted to collagen fragments containing the cross-linker 3-hydroxypyridinium. Furthermore, the above mentioned assays require tedious and complicated purifications from urine of collagen fragments containing 3-hydroxypyridinium to be used for the production of antibodies and for antigens in the assays.

At present very few clinical data using the approach described in U.S. Pat. No. 4,973,666 and U.S. Pat. No. 5,140,103 are available. Particularly, no data concerning the correlation between the urinary concentration (as determined by methods described in the above mentioned patents) of 3-hydroxypyridinium containing telopeptides of type I collagen and the actual bone loss (as determined by repeated measurements by bone densiometry) have been published. The presence of 3-hydroxypyridinium containing telopeptides in urine requires the proper formation in bone tissue of this specific cross-linking structure at various times before the bone resorbing process. Very little information on these processes is available and it would be desirable to avoid this dependence on the correct formation of the cross-linking structure.

GB Patent Application No. 2205643 reports that the degradation of type III collagen in the body can be quantitatively determined by measuring the concentration of an N-terminal telopeptide from type III collagen in a body fluid. This method uses antibodies generated to N-terminal telopeptides released by bacterial collagenase degradation of type III collagen, said telopeptides being labelled and used in the assay.

Schröter-Kermani et al., Immunol. Invest. 19:475–491 (1990) describe immunological measurement systems based on CNBr fragments of collagen type I and II. Use is made of pepsin-solubilised collagen, leaving the telopeptides in the tissue (cf. the above mentioned GB Patent Application No. 2205643).

The development of a monoclonal antibody raised against pepsin-solubilised type I collagen is described in Werkmeister et al., Eur. J. Biochem. 1987:439–443 (1990). The antibody is used for immunohistochemical staining of tissue segments and for measuring the collagen content in cell cultures. The measurements are not carried out on body fluids.

EP Patent Application No. 0505210 describes the development of antibody reagents by immunisation with purified cross-linked C-terminal telopeptides from type I collagen. The immunogen is prepared by solubilising human bone collagen with bacterial collagenase. The antibodies thus prepared are able to react with both cross-linked and non-cross-linked telopeptides, and cross-linkers other than pyridinoline.

International Patent Application No. WO 91/09114 discloses certain synthetic peptides which are used to promote cellular adhesion to a solid substrate. The use of the synthetic peptides as immunological reagents is not mentioned.

There are a number of reports indicating that collagen degradation can be measured by quantitating certain collagen propeptides. Propepcides are distinguished from telopeptides and the alpha-helical region of the collagen core by their location in the procollagen molecule and the timing of their cleavage in vivo; see U.S. Pat. No. 4,504,587; U.S. Pat. No. 4,312,853; Pierard et al., Analytical Biochemistry 141:127–136 (1984); Niemela, Clin. Chem. 31/8:1301–1304 (1985); and Rohde et al., European Journal of Clinical Investigation, 9:451–459 (1979).

EP Patent Application No. 0298210 and No. 0339443 both describe immunological determination of procollagen peptide type III and fragments thereof. Further, a method based on the measurement of procollagen is disclosed in EP Patent Application No. 0465104.

The use of synthetic peptides with sequences derived from type IX collagen for the development of immunological reagents is disclosed in PCT Patent Application No. WO90/08195. Likewise the application describes the use of the antibodies thus produced for the determination of type IX collagen fragments in body fluids.

U.S. Pat. No. 4,778,768 relates to a method of determining changes occurring in articular cartilage involving quantifying proteogylcan monomers or antigenic fragmemts thereof in a Dodge, J. Clin Invest 83:647–661 (1981) discloses methods for analysing type II collagen degradation utilising a polyclonal antiserum that specifically reacts with unwound alpha-chains and cyanogen bromide-derived peptides of human and bovine type II collagens. The degradation products of collagen were not detected in a body fluid, but histochemically by staining of cell cultures, i.e. by "in situ" detection.

WO94/03813 describes a competitive immunoassay for detecting collagen or collagen fragments in a sample wherein a binding partner containing a synthetic linear peptide corresponding to the non-helical C-terminal or N-terminal domain of collagen is incubated with an antibody to the linear synthetic peptide and the sample, and wherein the binding of the antibody to the binding partner is determined.

WO95/08115 relates to assay methods in which collagen fragments in a body fluid are determined by reaction with an antibody which is reactive with a synthetic peptide. The assay may be a competition assay in which the sample and such a peptide compete for an antibody, possibly a polyclonal antibody raised against fragments of collagen obtained by collagenase degradation of collagen. Alternatively, it may be an assay in which an antibody, possibly a monoclonal antibody, is used which has been raised against such a synthetic peptide.

One particular peptide fragment which we have found in body fluid, particularly urine, is of the formula:

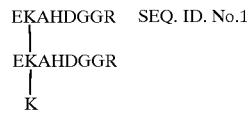

Formula 1

In the above formula, K—K—K represents cross-link which may for instance be a hydroxypyridinium cross-link but may be any naturally occurring cross-link and specifically any of those discussed in Last et al. Int. J. Biochem. Vol. 22, No. 6, 559–564, 1990.

A larger peptide fragment including the above smaller fragment is reported in EP 0394296.

In one bone resorption assay (CrossLaps™) described in WO95/08115, fragments of type I collagen containing a specific 8 amino acid sequence of the C telopeptide of type 1 collagen are quantitated (see also Bonde et al., Immunoassay for quanti-fying type I collagen degradation products in urine evaluated, Clin. Chem. 40/11, 2022–2025 (1994)—Endocrinology and Metabolism.

Another bone resorption assay (described in WO94/038113) relates to all fragments containing a pyridinoline structure and two peptide chains of the N-telopeptides of type I collagen (see also Hanson et al., A specific immunoassay for monitoring human bone resorption: quantitation of type 1 collagen cross-linked N-telopeptides in urine, Journal of Bone and Mineral Research, Vol. 7, Number 11, 1992). We believe the fragments reactive in both these assays to have a considerable variation in respect of their size and their content of crosslinking molecules (e.g. pyridinoline, Ehrlich chromogen, and pyrrole structures).

Various studies have been done comparing the results obtained using one prior art assay with those of another such assay on the same samples. The purpose of these studies has been to establish the reliability of these assays as measures of the rate of bone resorption, see for instance Garnero et al, Journal of Clinical Endocrinology and Metabolism, 70, No.3, 780–785.

Whilst studies of this type look for significance in the similarities of the results given by different assays, we believe that they fail to appreciate the valuable information regarding the origin and causes of bone resorption in individual patients which can be revealed by the differences in these results.

The exact fragmentation pattern of type I collagen in vivo is not yet fully elucidated. It has been shown, however, that the fragmentation pattern of type I collagen as measured by the pattern of reactivity in gelfiltration techniques is significantly different in women receiving one antiresorptive therapy when compared to women receiving another (Garnero et al. American Society of Bone and Mineral Research, Abstract 134, Kansas City, 1994). It has also been shown that the fragmentation pattern varies significantly in untreated women (unpublished observations).

We have now further established that these differences in fragmentation patterns are reflected in differences in results obtained using different immunological assays for bone collagen degradation products.

The present invention now provides a method of estimating the fragmentation pattern of collagen, preferably type 1 collagen, in a body fluid, comprising subjecting a sample of said body fluid to at least two distinct immunological assays, each of which measures the amount of a respective population of collagen breakdown products in said sample and comparing the results of the said measurements.

Thus, in a diagnosis situation, one may aim at measurements of the fragments of type I collagen which put more emphasis on those which may be of "pathological" nature and put less emphasis on the fragments generated in a "healthy" renewal of the skeleton.

It will be understood that the population of breakdown products detected by the respective assays may overlap. Indeed, one of said populations may be a sub-population which is wholly within the other said population.

The use of a comparison, e.g. by forming a ratio, between the concentration of specific fragments and the concentration of other fragments or the sum of fragments is highly relevant in this context as a high rate of bone resorption can probably occur in a "healthy" renewal of the skeleton, provided of course that the rate of bone formation also is high. As an example one assay could be used for measurement of the sum of degradation products whereas another would preferentially detect molecules generated during "normal" or "regular" collagen degradation. By creating the index between the two assays one will indirectly have information about the amount of collagen fragments generated by "pathological" collagen degradation, e.g. by bone metastasis. A parallel diagnostic relation exists in the area of estimating the risk of atherosclerosis. In this case the total cholesterol and subfractions of cholesterol in form of HDL and LDL are measured.

According to the invention, the results may preferably be compared by combining them mathematically to form a numerical index, e.g. by taking their ratio.

A ratio formed between the concentration of the fragments measured in two independent immunological assays of bone resorption, provides an index which is dependent on the fragmentation pattern of type I collagen and which therefore can be used for diagnostic purposes in relation to disorders associated to the metabolism of collagen.

A numerical index derived from two or more assays may be linked to a particular identified pattern of fragmentation if desired by separating collagen fragments in the sample, e.g. by HPLC or by gel-filtration, and measuring the amounts of peptide in specific fractions, optionally identifying the peptides in question. However, this is not necessary to the practice of the invention.

One may simply associate particular numerical index results with particular patient types. This may be done by subjecting a range of samples of known type to selected pairs or larger multiples of assays and building up a database of results. One may then identify the fragmentation pattern of an unknown sample as being typical of a particular class of sample previously tested. The term "patient type" embraces both healthy patients of different age and/or sex and patients with one or more pathological or abnormal conditions.

Preferably in accordance with the invention each of said populations of breakdown products comprises breakdown products of telopeptides of type I collagen.

Preferably at least one said population is of breakdown products containing peptides comprising one or more of the following amino acid sequences of human type 1 collagen:

Asp-Glu-Lys-Ser-Thr-Gly-Gly—SEQ. ID. No.2

Glu-Lys-Ala-His-Asp-Gly-Gly-Arg—SEQ. ID. No.3

Gln-Tyr-Asp-Gly-Lys-Gly-Val-Gly—SEQ. ID. No.4

Gly-Met-Lys-Gly-His-Arg—SEQ. ID. No.5

Gly-Ile-Lys-Gly-His-Arg—SEQ. ID. No.6

Gly-Phe-Lys-Gly-Ile-Arg—SEQ. ID. No.7

Gly-Leu-Pro-Gly-Leu-Lys-Gly-His-Asn—SEQ. ID. No.8

One such population may contain peptides comprising one or more of the following amino acid sequences of human type II collagen:

Glu-Lys-Gly-Pro-Asp—SEQ. ID. No.9

Gly-Val-Lys—SEQ. ID. No.10

Pro-Gly-Val-Lys-Gly—SEQ. ID. No.11

Pro-Gly-Pro-Lys-Gly-Glu—SEQ. ID. No.12

Gly-Gln-Lys-Gly-Glu-Pro—SEQ. ID. No.13 or Gly-Asp-Ile-Lys-Asp-Ile-Val—SEQ. ID. No. 14 or one or more of the following amino acid sequences of human collagen type III:

Asp-Val-Lys-Ser-Gly-Val—SEQ. ID. No. 15

Glu-Lys-Ala-Gly-Gly-Phe-Ala—SEQ. ID. No. 16

Gly-Phe-Pro-Gly-Met-Lys-Gly-His-Arg—SEQ. ID. No. 17 or Gly-Ala-Ala-Gly-Ile-Lys-Gly-His-Arg—SEQ. ID. No. 18

Similar sequences with isoaspartic acid replacing aspartic acid may be detected.

Preferably, one of said assays measures the amount of population of breakdown products characterised by containing isoaspartic acid.

Said population may comprise or consist of breakdown products containing one or more peptides of the sequence EKAH*GGR (SEQ. ID No. 19), wherein * is isoaspartic acid and K is part of a collagen cross-link or is lysine.

One of the assays may involve determining the amount of the peptide of formula 2 (below) present in said body fluid:

Formula 2

wherein K—K—K is any naturally occurring cross-link and * is isoaspartic acid, or of one or more peptides incorporating an epitope present in the peptide of formula 2 which contains isosparcic acid.

Said determination may be carried out using an immunological binding partner specific for an isoaspartic acid containing species present in the sample during the procedure.

The immunological binding partner may be an antibody raised against a linear peptide corresponding to a sequence within collagen with isoaspartic acid substituting in said amino acid sequence for aspartic acid in said collagen sequence. It may be an antibody raised against a fragment of collagen, selected for its affinity for such an isoaspartic acid containing peptide.

One of the assays may preferably measure a population of breakdown products containing peptides related to those detected in one of the other assay by the presence of aspartic acid in place of isoaspartic acid.

The invention includes a kit for use in estimating the fragmentation pattern of collagen type 1 in a body fluid, comprising an immunological binding partner for a first population of collagen type I breakdown products, an immunological binding partner for a second population of collagen type 1 breakdown products and optionally one or more assay kit ingredients selected from buffers, wash solutions, synthetic peptides, anti-idiotype antibodies, antibody-enzyme conjugates, substrates for antibody-enzyme conjugates, body fluid control samples, standard solutions and enzyme conjugate reaction stopping solutions.

In accordance with a particularly preferred practice of the invention, we have found that specific fragmentation patterns of type I collagen, as determined in urine samples of gelfiltration techniques, can be estimated by forming a ratio between results obtained using two immunological assays, both assays being assays of bone resorption and both measuring degradation products of type I collagen. A first of the assays is based on a polyclonal antibody and is described in Bonde et al., Immunoassay for quantifying type I collagen degradation products in urine evaluated, Clin. Chem. 40/11, 2022–2025 (1994)—Endocrinology and Metabolism. The second assay is based on a monoclonal antibody and is described in Fledelius et al., American Society of Bone and Mineral Research, Abstract C 344, Kansas City, 1994). Both of these assays are also described in WO 95/08115.

It is observed, using gelfiltration experiments on urine samples, that the degradation of type I collagen varies from individual to individual not only in a quantitative manner but also in a qualitative manner. In order to express the qualitative differences in the degradation of type I collagen in a quantitative manner, a ratio may be formed between the results obtained in each of the above mentioned assays detecting different degradation fragment of type I collagen.

This ratio can be used for distinguishing between urine samples giving identical readings in one or other assay (see Table 1), and therefore has utility for diagnostic purposes.

It is contemplated that the method of forming the relevant ratio between assays of bone resorption will be used to diagnose disorders of the metabolism of collagen analogously to the diagnosis and estimation of risk of atherosclerosis, namely by measuring the total cholesterol and subfractions (HDL, LDL) and by forming the relevant ratios between the subfractions and the total cholesterol.

In brief the assays referred to above are based on an immobilised synthetic peptide with an amino acid sequence found in a part of the C-terminal telopeptide of the αI chain of type I collagen (Glu-Lys-Ala-His-Asp-Gly-Gly-Arg= 8AA SEQ. ID. No. 3).

To produce the polyclonal antibody used in the first assay, rabbits were immunised with collagenase treated collagen and antibody serums reactive with 8AA were selected.

To produce the monoclonal antibody of the second assay rabbits were immunised with 8AA conjugated to BSA using a two step carbodiimide procedure.

For coating of microtiter plates and 8AA peptide was conjugated to thyroglobulin using glutaraldehyde (Soinila S, Mpitsos G J, Soinila J. Immunchistochemistry of encephalins: Model studies on hapten-carrier conjugates and fixation methods. J. Hitochem Cytochem 1992:2:231–9). During incubation of samples with these antibodies a competition takes place between the immobilised peptide and the breakdown products of type I collagen in urine. As the content of the peptide in the solution increases, less antibody will bind to the immobilised peptide leading to a decreasing optical density.

Surprisingly it has been found that whilst the monoclonal antibody successfully detects peptides in urine containing all or some of the 8AA sequence, the polyclonal antibody under assay conditions selectively detects in urine peptides containing all or some of an analogous amino acid sequence in which isoaspartic acid replaces aspartic acid in the 8AA sequence (iso-8AA). In place of such a polyclonal antibody one may therefore use a polyclonal antibody selected for reactivity with the iso-8AA peptide or a monoclonal antibody raised against iso-8AA.

Thus, we have now discovered that a proportion of the peptide fragments in body fluid are related to peptides of equivalent formula, e.g. peptides of formula 1, by their replacement of aspartic acid in the formula by isoaspartic acid.

The isomerization of aspartic acid has been reported previously to be a spontaneous reaction occurring under physiological conditions.

See for instance Brennan et al. Protein Science 1993, 2, 331–338, Galletti et al., Biochem. J. 1995, 306, 313–325, Lowenson et al., Blood Cells 1988, 14, 103–117 and Oliya et al., Pharmaceutical Research, Vol. 11, No. 5, 1994, p.751.

The above discovery indicates that this isomerization also occurs in bone-issue and the extent of isomerization is expected therefore to be marker for the age of the bone tissue concerned.

Furthermore, the presence in such bone peptide fragments of the isomerization provides confirmation that the peptide fragments indeed derive from bone degradation and not some other source such as the degradation of newly formed collagen never incorporated into bone.

Preferably, therefore one of the assays is carried out using an immunological binding partner specific for an isoaspartic acid containing species present in the sample during the procedure, preferably said peptide of formula 2 or a peptide incorporating an epitope present in the peptide of formula 2 which contains isoaspartic acid.

The immunological binding partner may be a monoclonal or polyclonal antibody. By the requirement that the immunological binding partner be specific for the isoaspartic acid containing species is meant that the immunological binding partner distinguishes between said species and the analogous spartic acid containing species to an extent useful in the assay.

Suitable immunological binding partners also include fragments of antibodies capable of binding the same antigenic determinant including Fab, Fab' and F(ab')$_2$, fragments.

Preferably, the immunological binding partner is an antibody raised against a linear peptide, preferably a synthetic peptide, corresponding to a sequence within collagen with isoaspartic acid substituting in said amino acid sequence for aspartic acid in said collagen sequence Each assay may take many forms including ELISA, RIA, or IRMA, procedures for which are too well known to warrant description here.

In an ELISA of this type, the synthetic peptide may be immobilised on a solid support. A sample may be incubated with a polyclonal antibody or monoclonal antibody for the synthetic peptide in contact with the solid support and after washing, a peroxidase-conjugated (revealing) antibody may be added. After further incubation, a peroxidase substrate solution is added. By competition, peptides in the sample reactive with the antibody inhibit the peroxidase reaction.

Where the synthetic peptide is used to raise a monoclonal immunological binding partner, the synthetic peptide need not be a competing agent in the assay. For instance, collagenase treated collagen may be purified and immobilised onto the solid support and an ELISA may be carried out using a monoclonal antibody.

Antibodies may be prepared which are respectively selective for one or more aspartic acid containing peptides and for their isoaspartic acid containing analogues. It is then possible to carry out an assay for both variants of the peptide or peptides. The relative amount of isoaspartic acid will provide an indication of the age of the bone which is being broken down. Accordingly, the invention provides a method of obtaining information regarding collagen resorption in a patient, comprising measuring in a body fluid the relative amounts of at least one aspartic acid containing peptide derived from collagen and a corresponding isoaspartic acid containing peptide.

The invention may be applied both to humans and to animals.

Suitable body fluids include, e.g. human, urine, blood, serum, plasma and synovial fluid. It is contemplated that the method may also be used e.g. on saliva and sweat. The body fluid may be used as it is, or it may be purified prior to the contacting step. This purification step may be accomplished using a number of standard procedures, including, but not limited to, cartridge adsorption and elution, molecular sieve chromatography, dialysis, ion exchange, alumina chromarography, hydroxyapatite chromatography, and combinations thereof.

The invention is described in more detail below. Reference is made to the appended drawings, in which.

Figure 1:
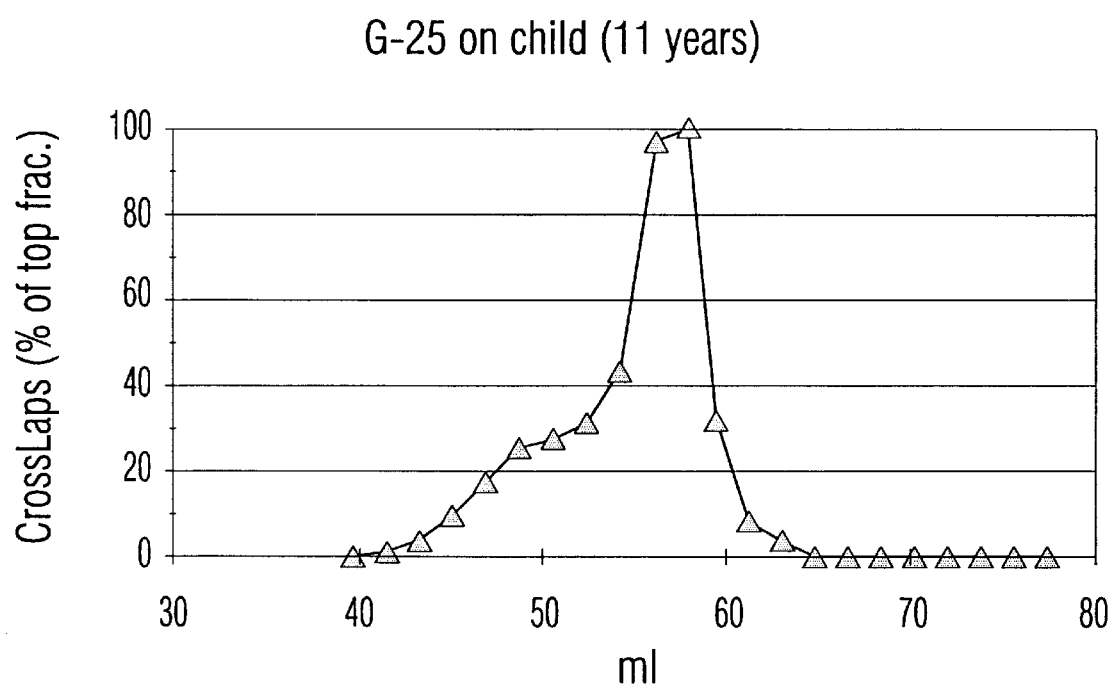
FIG. 1 shows the immunological reactivity of fractions of urine from a child of 11 years separated by gel filtration chromatography.
Figure 2:
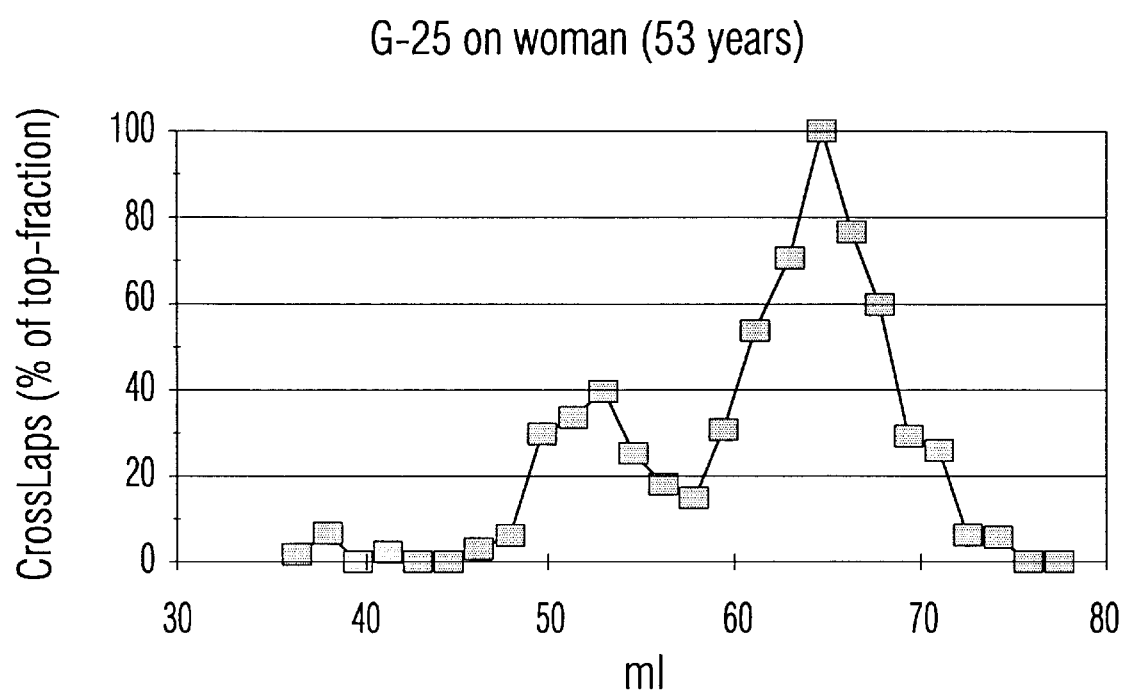
FIG. 2 shows similar results from a woman of 53.

In preferred embodiments of methods according to the invention, one or both assays are performed by an inhibition ELISA (enzyme linked immunosorbent assay) by contacting a sample with a synthetic peptide having a sequence derived from collagen and with an antibody, which is immunoreactive with the synthetic peptide. The synthetic peptide is immobilised on a solid support. The antibody may be raised against the synthetic peptide or raised against collagen degradation products and screened for by use of such a synthetic peptide.

The preparation of synthetic peptides may be performed according to procedures well known in the art, e.g. by solid-phase peptide synthesis techniques commonly described as "Merrifield synthesis". Also classical solution phase techniques may be used. Sequences of interest include potential sites for collagen cross-linking (see for example Kuhn, K., in Immunochemistry of the extracellular matrix, 1:1–29(1982), Eyre, D. R., Ann. Rev. Biochem. 53:717–48 (1984), or U.S. Pat. No. 5,140,103). Examples of such peptides sequences are given above.

Regarding the synthetic peptides, it is possible to omit (or add) one or more amino acid residues from (or to) the crosslinkable site sequences without substantial loss of the ability to (a) raise antibodies recognising the isoaspartic acid analogue of the corresponding native collagen fragment or (b) inhibit the binding of such antibodies to the said analogue of the native fragment. It is possible to use longer collagen fragments and/or chimeric peptides to raise the antibodies and, in principle, it is not necessary to use the same peptide as the immunogen and the competitor in a competition assay.

The methods for preparation of both monoclonal and polyclonal antibodies are well known in the art. For example, see Campbell, A. M., Laboratory Techniques in Biochemistry and Molecular Biology, Vol. 12 (1986). It is possible to produce antibodies to synthetic peptides by immunisation. However, because of the relatively small molecular weight of these compounds it is preferred that the hapten be conjugated to a carrier molecule. Suitable carrier molecules include, but are not limited to, bovine serum albumin, thyroglobulin, ovalbumin, tetanus toxoid, and keyhole limpet hemocyanin. The preferred carrier is bovine serum albumin. To present the hapten in its most immunogenic form to the antibody producing cells of the immunised animal a number of alternative coupling protocols can be used. Suitable procedures include, but are not limited to, glutaraldehyde carbodiimide, and periodate. Preferred binding agents are glutaraldehyde and carbodiimide.

The preparation of antibodies may be carried out by conventional techniques including immunisation with collagen fragments or synthetic peptides conjugated to a carrier. To improve the immunogenicity it is preferred that the immunogen be mixed with an adjuvant before injection. Examples of adjuvants include, but are not limited to, alulminium hydroxide, Freund's adjuvant, and immune-stimulating complexes (ISCOMs). ISCOMs can be made according to the method described by Morein, B. et al., Nature 308:457–460 (1984).

Either monoclonal or polyclonal antibodies to the hapten on carrier molecule can be produced. For the production of monoclonal antibodies it is preferred that mice are immunised. Spleen cells from the immunised mouse are harvested, homogenised, and thereafter fused with cancer cells in the presence of polyethylene glycol to produce a cell hybrid which produces monoclonal antibodies specific for peptide fragments derived from collagen. Suitable cancer cells include, but are not limited to, myeloma, hepatoma, carcinoma, and sarcoma cells. Detailed descriptions of the production of monoclonal antibodies are provided in Goding, J. W., in Monoclonal Antibodies: Principles and Practice, (1986). A preferred preliminary screening protocol comprises the use of synthetic peptides conjugated to a carrier and coated on to the solid surface of a microtiter plate.

For the preparation of polyclonal antibodies, which are reactive with peptide fragments derived from collagen, different animal species can be immunised. Suitable species include, but are not limited to, chicken, rabbit and goat. Chicken and rabbit are preferred.

Antibodies so produced may be screened for suitability for use according to the invention by testing for reactivity with an isoaspartic acid containing synthetic peptide of appropriate sequence.

Antibody fragments are prepared by methods known in the art (see E. Ishikawa. Journal of Immunoassay 3:209–327 (1983)).

Accordingly, by utilisation of an immunoassay with the antibodies prepared as above it is possible to assay a biological fluid sample without prior fractionation or hydrolysis. The specificity for the desired collagen in the biological fluid may be supplied by the antibody in combination with the use of a synthetic peptide (against which the antibody was raised or in any event with which the antibody is immunochemically reactive) in the assay construction.

As an alternative the immunoassay may be performed using a monoclonal antibody. The basic idea of this assay design is to shift the specificity of the assay from the antigen (synthetic peptide to collagen) to the antibody (from rabbit antiserum to monoclonal antibody). Using this construction the assay does not need to make further use of a synthetic peptide. This version of the immunoassay is suitably performed by incubating the patient sample or a standard solution with a peroxidase-conjugated antibody solution in a microtiter plate pre-coated with purified collagenase-treated collagen. After washing, the wells of the plate are incubated in the dark with a substrate solution. The colour reaction is stopped by the addition of a stopping solution, and finally the absorbance is measured.

The immunoassays themselves may be conducted using any procedure selected from the variety of standard assay protocols generally known in the art. As it is generally understood, the assay is constructed so as to rely on the interaction between the specific immunological binding partner and the desired analyte for specificity and to utilise some means to detect the complex formed by the analyte and the immunological binding partner. The immunological binding partner may be complexed to a solid support and used as a capture immunological binding partner for the analyte. This protocol may be run in a direct form, wherein the formation of analyte-immunological binding partner complex is detected, e.g. by a fluorescent, radioactive or enzymatic label, or it may be run in a competitive format wherein a labelled standard competes with the analyte for the immunological binding partner. The format may also be constructed as an agglutination assay or the complex may be precipitated by addition of a suitable precipitant to the reaction mixture. The specific design of the immunoassay protocol is open to a wide variety of choice, and the number of clinical assay devices and protocols available in the art is multitudinous. For a variety of such protocols, see U.S. Pat. No. 5,001,225.

The antibodies and revealing reagents for the conduct of an immunoassay using standard detection protocols, for example radioisotope labelling, fluorescent labelling or ELISA, either in a direct or competitive format, may conveniently be supplied as kits which include the necessary components and instructions for the assay. In one embodiment of the invention such a kit includes a microtiter plate coated with a relevant synthetic peptide, standard solutions for preparation of a standard curve, a urine or other body fluid control for quality testing of the analytical run, rabbit antibodies reactive with the above mentioned synthetic peptide, anti-rabbit immunoglobulins conjugated to peroxidase, a substrate solution, a stopping solution, a washing buffer and an instruction manual.

Since immunoassays can be constructed using antibodies and specific synthetic peptides, the ratios of the corresponding collagen fragment sequences in an appropriate biological fluid can be determined as well as their individual levels and their total. Thus, the assay can be designed to include antibodies which will result in determination of several isoaspartic acid containing peptides and optionally the native peptide sequences or determination of a single isoaspartic acid containing peptide sequence and a corresponding or different native peptide sequence, or any desired combination thereof.

The following examples are intended to illustrate, but not to limit the invention.

General

For the practical performance of the assays described in the following examples, 15 µl Standard or unknown sample was pipetted in duplicates into the appropriate wells in the pre-coated ELISA plate. Then 100 µl Antibody Solution was added to each well, the plate was covered with sealing tape and incubated at room temperature for 60 min on a shaking device. All the following procedures were also carried out at room temperature. After incubation the plates were washed three times with diluted Washing Buffer.

Peroxide conjugated Antibody (HRP-conjugated goat antibodies to rabbit IgG, 100 µl/well) was added and the sealed wells were incubated 60 min on a shaking device. Following another washing procedure, 100 µl of TMB Substrate Solution was added to all wells which were sealed and incubated for 15 min. The enzyme reaction stopped after 15 min by addition of 100 µl Stopping Solution. The optical density was read in an ELISA-reader at 450 nm.

A calibration curve was constructed on a log-linear graph paper by plotting the mean absorbances of the five standards (0.1–5.0 µg/ml). The concentration of equivalents to the synthetic peptide (Glu-Lys-Ala-His-Asp-Gly-Gly-Arg; SEQ. ID No. 3) in each patient specimen were determined by interpolation on the calibration curve.

The pipetting scheme as well as the incubations and washing steps for the assay employing the monoclonal antibody (ASbAY) was the same as for the assay employing the polyclonal antibody.

EXAMPLE 1

Gelfiltration of Urine From Children and Adult Women

One urine sample from a child (age: 11 years) and one urine sample from a women (age: 53 years) were applied to respective gelfiltration columns 0.75 ml of urine was injected into the identical 900×10 mm columns containing 58 ml of G25 Sephadex superfine gel (Pharmacia, Uppsala, Sweden.). Elution was performed at a 0.22 ml/min flow rate, using a 25 mol/l phosphate buffer of pH 7.4 and was monitored with a 280 nm UV detector. The collected fractions (1.6–1.8 ml per fraction) were analysed in the Cross-Laps™ ELISA (Bonde et al., Clin. Chem. 40/11, 2022–2025 (1994)—Endocrinology and Metabolism).

As can be seen from FIG. 1, the urine from the child of 11 years shows only one major peak after approximately 56 ml. When looking at the elution profile from urine from the woman (age: 53 years), two distinct peaks are observed (first peak at 53 ml and peak 2 at 64 ml). These observations indicate that there is a difference in the distribution of the fragments of type I collagen between the subjects. It appears that the urine from the child is deficient in the smaller fragments as this urine is lacking the second peak found at 64 ml in the urine of the adult woman.

EXAMPLE 2

Immunoassays on Urine Samples From Children and Adult Women

Urine samples from 8 women (age 23–56) and 8 children (age 8–12) were analysed in the two immunoassays, one polyclonal and one monoclonal described above. Table 1 shows the results of each urine sample. Furthermore, it gives the ratio of the values obtained in the two systems on one sample. The values from the children all are in the range 0.82–1.12, whereas the values for the adult women are in the range 0.14–0.25. Each value given in the table is based on three independent tests in the two assays.

TABLE 1

| Sample ID | Poly (µg/ml) | Mono (µg/ml) | Ratio (mono/poly) |
|---|---|---|---|
| Child #1 | 4.14 | 4.05 | 0.98 |
| Child #2 | 8.12 | 8.87 | 1.09 |
| Child #3 | 3.22 | 3.28 | 1.02 |
| Child #4 | 1.23 | 1.09 | 0.89 |
| Child #5 | 3.40 | 2.79 | 0.82 |
| Child #6 | 2.12 | 1.90 | 0.86 |
| Child #7 | 1.45 | 1.51 | 1.04 |
| Child #8 | 6.03 | 5.49 | 0.91 |
| Woman #1 | 4.14 | 0.79 | 0.19 |
| Woman #2 | 6.12 | 0.98 | 0.16 |
| Woman #3 | 1.88 | 0.47 | 0.25 |
| Woman #4 | 5.22 | 0.83 | 0.16 |
| Woman #5 | 2.76 | 0.66 | 0.24 |
| Woman #6 | 5.04 | 0.71 | 0.14 |
| Woman #7 | 7.45 | 1.42 | 0.19 |
| Woman #8 | 4.76 | 0.86 | 0.18 |

EXAMPLE 3

Paget's Disease

The same two immunoassays were used on samples from known Paget's disease patients and control. The results in Table 2 below show that the differing fragmentation patterns produce ratios that enable the samples to be distinguished.

TABLE 2

| CONTROLS SAMPLE No. | CROSSLAPS (MG/L) | MABA7 (MG/L) | RATIO MABA7/CROSS |
|---|---|---|---|
| 1 | 4.14 | 0.79 | 0.19 |
| 2 | 6.12 | 0.98 | 0.16 |
| 3 | 1.88 | 0.47 | 0.25 |
| 4 | 5.22 | 0.83 | 0.16 |
| 5 | 2.76 | 0.66 | 0.24 |
| 6 | 5.04 | 0.71 | 0.14 |
| 7 | 7.45 | 1.42 | 0.19 |
| 8 | 4.76 | 0.86 | 0.18 |
| MEAN | | | 0.19 |

| PATIENTS SAMPLE No. | CROSSLAPS (MG/L) | MABA7 (MG/L) | RATIO MABA7/CROSS |
|---|---|---|---|
| 1 | 0.79 | 0.63 | 0.80 |
| 2 | 26.37 | 49.96 | 1.89 |
| 3 | 12.24 | 4.61 | 0.38 |
| 4 | 1.97 | 2.97 | 1.51 |
| 5 | 24.33 | 78.74 | 3.24 |
| 6 | 5.53 | 9.95 | 1.80 |
| MEAN | | | 1.60 |

CROSSLAPS = polyclonal
MABA7 = monoclonal

EXAMPLE 4
Breast Cancer With Secondary Bone Metastasis

Figure 3:
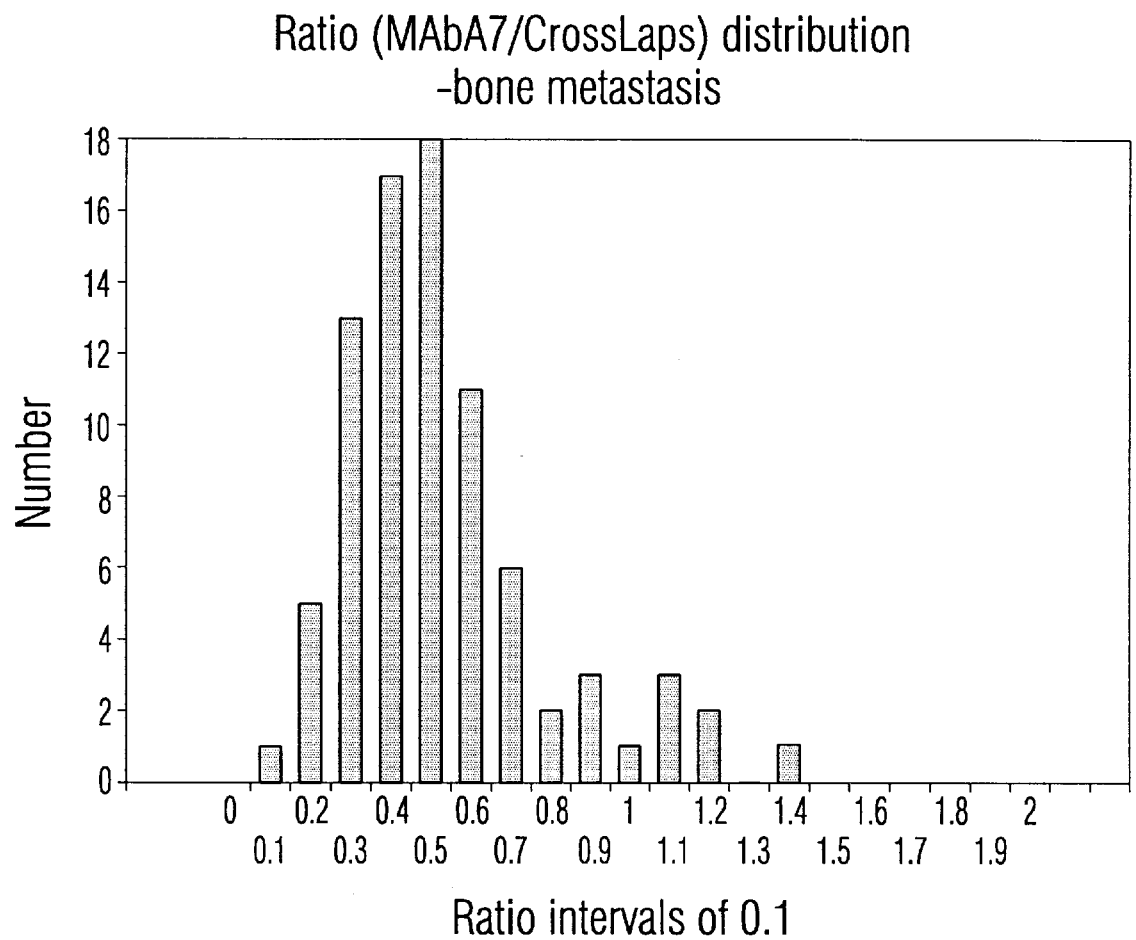
FIG. 3 is a histogram of the results obtained in Example 4 for cancer patients.
Figure 4:
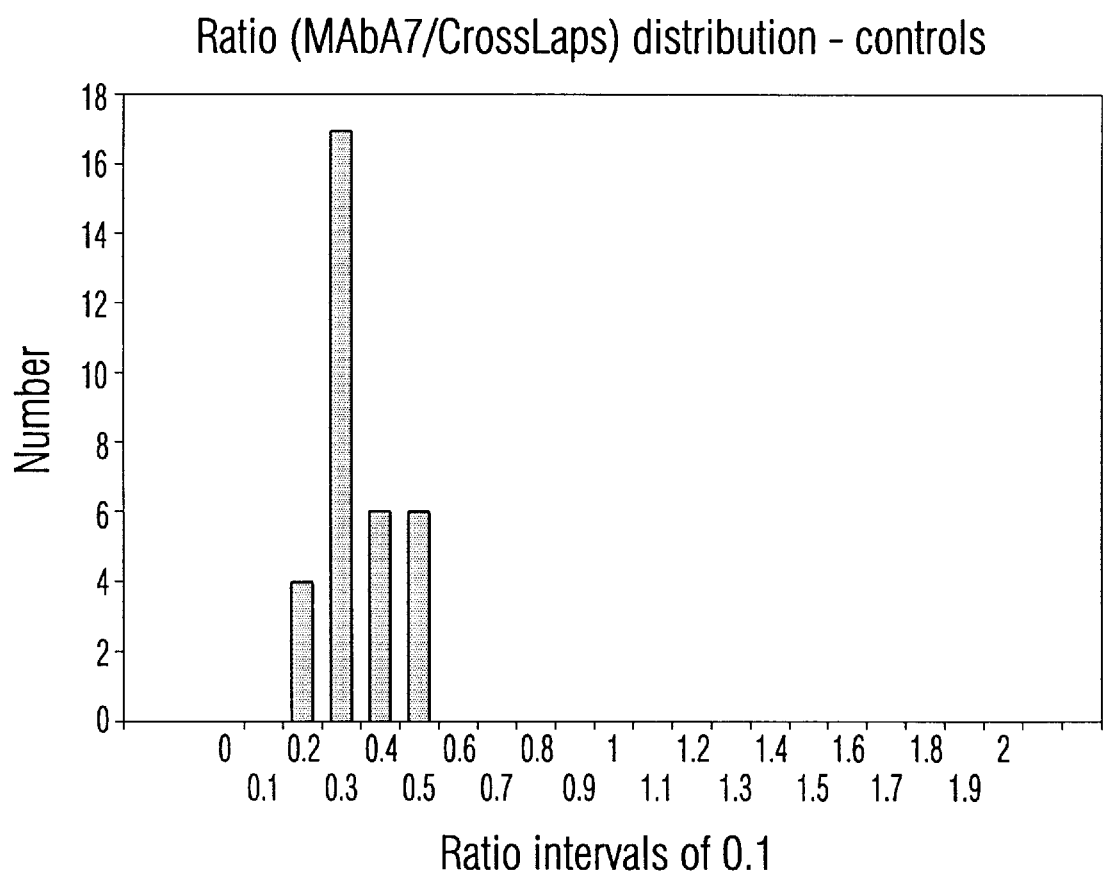
FIG. 4 shows equivalent results for controls.

The assays used in Example 3 were run on urine samples from patients suffering from breast cancer with secondary bone metastasis and on healthy patient controls. The ratio of the results for the healthy population was found to be from 0.1 to 0.4 whereas 50% of the samples from bone metastasis patients had a ratio of greater than 0.4. The results are shown in FIGS. 3 and 4.

---

What is claimed is:

1. A method of characterizing the degradation of type 1 collagen in a body fluid, comprising:

(a) subjecting a sample of body fluid to at least two distinct immunological assays, wherein a first assay comprises measuring the amount of a first population of type I collagen breakdown products present in the sample by contacting the sample with a first immunological binding partner which binds to said first population, and a second assay comprises measuring the amount of a second population of type I collagen breakdown products present in the sample by contacting the sample with a second immunological binding partner which binds to said second population; and (b) forming a numerical index representing the difference in the results of said measurements, which index serves to characterize said degradation;

wherein each of said first and second populations comprises Glu-Lys-Ala-His-Asp-Gly-Gly-Arg (SEQ ID NO:3), an isoaspartic derivative of Glu-Lys-Ala-His-Asp-Gly-Gly-Arg (SEQ ID NO:3); or a mixture thereof.

2. A kit for use in characterizing the degradation of collagen type I in a body fluid, comprising a first immunological binding partner which binds to a first population of type I collagen breakdown products, a second immunological binding partner which binds to a second population of type I collagen breakdown products and optionally one or more assay kit ingredients selected from buffers, wash solutions, synthetic peptides, anti-idiotype antibodies, antibody-enzyme conjugates, substrates for antibody-enzyme conjugates, body fluid control samples, standard solutions and enzyme conjugate reaction stopping solutions; wherein each of said first and second populations comprises Glu-Lys-Ala-His-Asp-Gly-Gly-Arg (SEQ ID NO:3), an isoaspartic derivative of Glu-Lys-Ala-His-Asp-Gly-Gly-Arg (SEQ ID NO:3); or a mixture thereof.

* * * * *

UNITED STATES PATENT AND TRADEMARK OFFICE
CERTIFICATE OF CORRECTION

PATENT NO.    : 6,210,902 B1
DATED         : April 3, 2001
INVENTOR(S)   : Martin Bonde et al.

Page 1 of 1

It is certified that error appears in the above-identified patent and that said Letters Patent is hereby corrected as shown below:

Title page,
Item [30], should read
-- [30] Foreign Application Priority Data

October 17, 1994    DK1194/94
    March 24, 1995    GB 9506050.5 --

Signed and Sealed this

Thirtieth Day of April, 2002

Attest:

*Attesting Officer*

JAMES E. ROGAN
*Director of the United States Patent and Trademark Office*

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: C-terminal (vi) ORIGINAL SOURCE:
      (A) ORGANISM: Homo sapien
      (F) TISSUE TYPE: Collagen (ix) FEATURE:
      (A) NAME/KEY: Other
      (B) LOCATION: 2
      (D) OTHER INFORMATION: Cross-link to lysine residue at
          position 2 of identical second chain (xi) SEQUENCE DESCRIPTION: SEQ ID NO:1:

Glu Lys Ala His Asp Gly Gly Arg
1               5

(2) INFORMATION FOR SEQ ID NO:2:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Asp Glu Lys Ser Thr Gly Gly
1               5

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Glu Lys Ala His Asp Gly Gly Arg
1               5

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Gln Tyr Asp Gly Lys Gly Val Gly
1               5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Gly Met Lys Gly His Arg
1               5

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Gly Ile Lys Gly His Arg (2) INFORMATION FOR SEQ ID NO:7:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:7:

Gly Phe Lys Gly Ile Arg
1               5

(2) INFORMATION FOR SEQ ID NO:8:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:8:

Gly Leu Pro Gly Leu Lys Gly His Asn
1               5

(2) INFORMATION FOR SEQ ID NO:9:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:9:

Glu Lys Gly Pro Asp
1               5

(2) INFORMATION FOR SEQ ID NO:10:

(i) SEQUENCE CHARACTERISTICS:
       (A) LENGTH: 3 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:10:

Gly Val Lys
1

(2) INFORMATION FOR SEQ ID NO:11:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:11:

```
Pro Gly Val Lys Gly
1               5
```

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Pro Gly Pro Lys Gly Glu
1               5
```

(2) INFORMATION FOR SEQ ID NO:13:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Gly Gln Lys Gly Glu Pro
1               5
```

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Gly Asp Ile Lys Asp Ile Val
1               5
```

(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Asp Val Lys Ser Gly Val
1               5
```

(2) INFORMATION FOR SEQ ID NO:16:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Glu Lys Ala Gly Gly Pro Ala
1               5
```

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Gly Phe Pro Gly Met Lys Gly His Arg
1               5
```

(2) INFORMATION FOR SEQ ID NO:18:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Gly Ala Ala Gly Ile Lys Gly His Arg
1               5
```

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 2
        (D) OTHER INFORMATION: Lysine may be part of a collagen
            cross-link
        (A) NAME/KEY: Other
        (B) LOCATION: 5
        (D) OTHER INFORMATION: Beta-Aspartic Acid (xi) SEQUENCE DESCRIPTION: SEQ ID NO:19:

```
Glu Lys Ala His Xaa Gly Gly Arg
1               5
```

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 2
        (D) OTHER INFORMATION: Cross-link to lysine residue at
            position 2 of identical second chain
        (A) NAME/KEY: Other
        (B) LOCATION: 5

```
            (D) OTHER INFORMATION: Beta-Aspartic Acid (xi) SEQUENCE DESCRIPTION: SEQ ID NO:20:

Glu Lys Ala His Xaa Gly Gly Arg
1               5
```